| United States Patent [19]
Hartog et al. | [11] Patent Number: 4,889,852 |
| --- | --- |
| | [45] Date of Patent: Dec. 26, 1989 |

[54] ANXIOLYTICALLY ACTIVE PIPERAZINE DERIVATIVES

[75] Inventors: Jan Hartog; Johannes Mos, both of Weesp, Netherlands

[73] Assignee: Duphar International Research B.V., Weesp, Netherlands

[21] Appl. No.: 241,311

[22] Filed: Sep. 7, 1988

[30] Foreign Application Priority Data

Sep. 11, 1987 [NL] Netherlands ......................... 8702167

[51] Int. Cl.$^4$ ..................... A61K 31/47; A61K 31/50; A61K 31/415; A61K 31/425; A61K 31/495; A61K 31/535

[52] U.S. Cl. ................................. 514/230.5; 514/248; 514/249; 514/253; 514/255; 514/314; 514/365; 514/385

[58] Field of Search ............... 514/249, 248, 253, 255, 514/314, 365, 385

Primary Examiner—Stanley J. Friedman
Attorney, Agent, or Firm—Stevens, Davis, Miller & Mosher

[57] ABSTRACT

It has been found that a group of piperazine derivatives known to have blood-pressure lowering properties possess good anxiolytic properties. In two well known animal test models the compounds are active when used intraperitoneally in dosages of 0.3 mg/kg.

2 Claims, No Drawings

ANXIOLYTICALLY ACTIVE PIPERAZINE DERIVATIVES

The invention relates to a new application of known piperazine derivatives.

It has been found that the piperazine derivatives known from European Patent Application Nos. 0138280 and 0185429 of the general formula 1

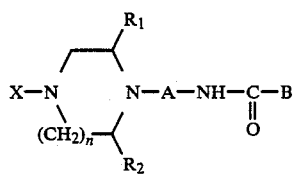

1.

wherein
$R_1$ and $R_2$ independently of each other represent hydrogen or an alkyl group having 1-3 carbon atoms,
n has the value 1 or 2,
X is one of the groups of the formula 2-22,

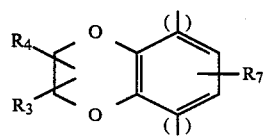

2.

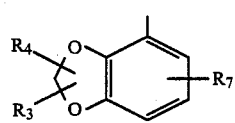

3.

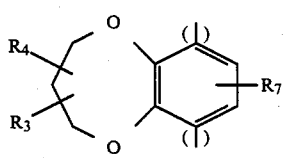

4.

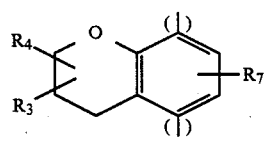

5.

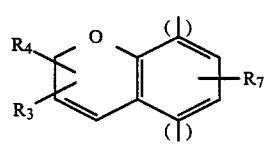

6.

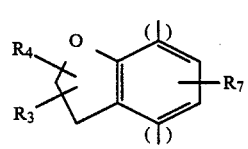

7.

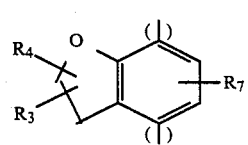

8.

-continued

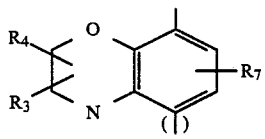

9.

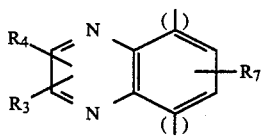

10.

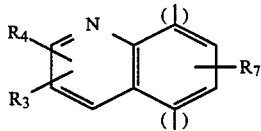

11.

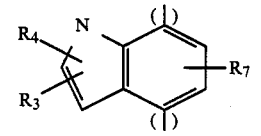

12.

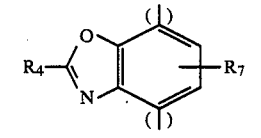

13.

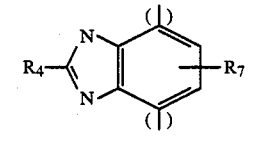

14.

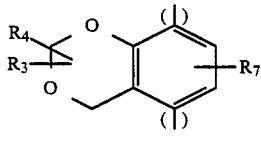

15.

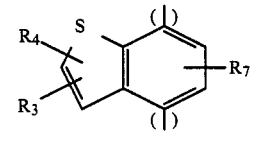

16.

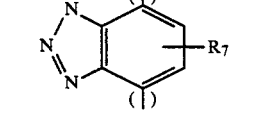

17.

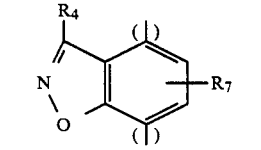

18.

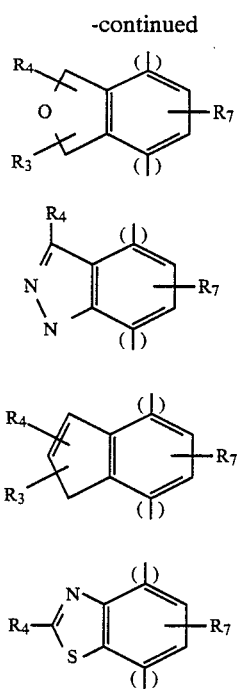

with the proviso that the groups of the formulae 2, 5, 6, 9, 10, 11 and 15 may be bound to the nitrogen atom of the piperazine group via position 5 or 8, the group of formula 4 may be bound to the nitrogen atom of the piperazine group via position 6 or 9, and the groups of the formulae 7, 8, 12, 13, 14 and 16–22 may be bound to the nitrogen atom of the piperazine group via position 4 or 7, in which groups $R_3$ represents hydrogen or straight or branched alkyl having 1–3 carbon atoms, $R_4$ represents hydrogen, halogen, alkyl having 1 to 3 carbon atoms, methylene, ethylidene or vinyl, a straight or branched hydroxyalkyl group having 1–3 carbon atoms, which may optionally be etherified or esterified, or an alkylcarbonyl group having 1–3 carbon atoms in the straight or branched alkyl group, an oxo group or a phenyl group, and $R_7$ is a hydrogen atom or a fluorine atom, A is a straight or branched alkylene group having 2–10 C-atoms, B is an aryl group or a heteroaryl group which may be substituted with one or more of the following substituents: halogen, trifluoromethyl, nitrile, alkoxy having 1–3 C-atoms, hydroxy, esterified hydroxy, or alkyl having 1–2 C-atoms, or wherein B is a straight or branched alkyl group or a saturated or partly unsaturated cycloalkyl group having 4–10 carbon atoms, prodrugs and salts thereof with pharmaceutically acceptable acids have good anxiolytic properties.

Prodrugs are derivatives from which after administration an active substance of formula 1 is released.

When one or more optically active carbon atoms occur in the compounds of formula 1, the invention relates both to the use of the individual enantiomers and of the racemates.

The above-defined group of compounds of formula 1 have been described to have a hypotensive activity.

It has surprisingly been found that the compounds of formula 1 have psychotropic properties, notably an interesting anxiolytic activity.

The anxiolytic activity was established in a number of animal models known and suitable for this purpose.

(1) It is known that young rats which are isolated from their mother and their nest-mates produce ultrasonic sounds, so-called pup vocalisations (see Biochem. Behav. 24, (1986), 1263–1267). These pup vocalisations are characterized as a natural reaction and can be inhibited by means of anxiolytics. In contrast with other models, removal of a previously caused behaviour inhibition is not involved in this anxiety test.

(2) In a second animal model the animal behaviour is used which is recorded after having inflicted a stimulus of a more or less unpleasant nature; for example, the natural aversion of rats to light or electric shocks. Such stimuli cause an inhibition of certain behaviour elements and lead to avoiding the undesired situation. Compounds having an anxiolytic activity remove the said inhibition (see Biochem. Behav. 13, (1980), 167–170 and Eur. J. Pharmacol. 4, (1968), 145–151).

(3) It is known (see Neuropsychobiology 18, (1987), 51–56, F. Krijzer and R. van de Molen) that clinically effective anxiolytcs cause an electroencephalogram (EEG) which is characteristic for these substances.

The compounds having formula 1 are active in the models (1) and (2) and cause EEG's which show a great resemblance with the EEG's caused by clinically active anxiolytics.

The compounds according to the invention are active in dosages which as a rule are between 0.1 and 100 mg/kg after oral administration.

On the basis of the found anxiolytic activity the compounds of formula 1 are suitable for the treatment of syndromes in which fear or fear symptoms, for example in certain forms of compulsive behaviour, obsessions, phobias and panic, are involved.

The compounds can be brought into a form of administration suitable as an anxiolytic for human application, i.e. can be formulated to compositions suitable for this purpose and to be administered orally by preference.

EXAMPLE

The compounds 4-fluoro-N-[2-[4-[5-(1,4-benzodioxanyl]-1-piperazinyl]-ethyl]benzamide and (+)-4-fluoro-N-[2-[4-[5-(2-hydroxymethyl-1,4-benzodioxanyl)]-1-piperazinyl]-ethyl]benzamide significally reduced fear in the above described test models (1) and (2), when used in dosages of 0.3 mg/kg (intraperitoneal) and higher.

We claim:

1. A method of treating syndromes in which fear or fear symptoms are involved, characterized in that an anxiolytically effective amount of a compound of the formula:

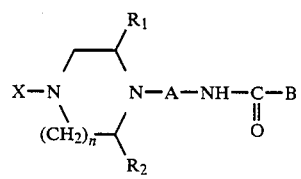

wherein $R_1$ and $R_2$ independently of each other are hydrogen or an alkyl having 1 to 3 carbon atoms;
n is 1 or 2;
X is selected from the group consisting of:

2.
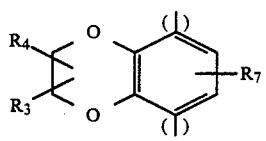
3.
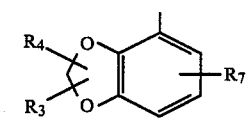
4.
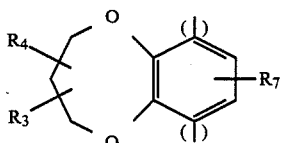
5.
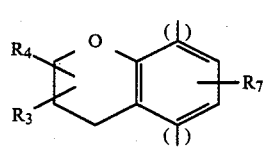
6.
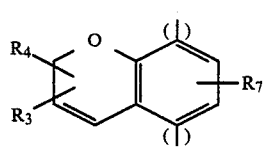
7.
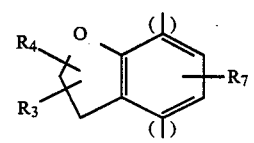
8.
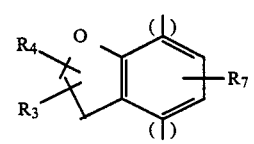
9.
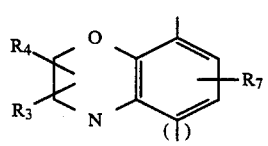
10.
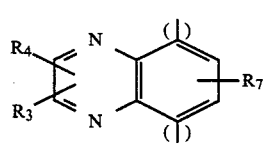
11.
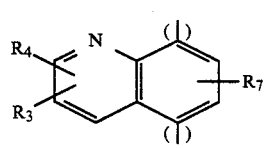
12.
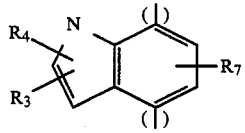
13.
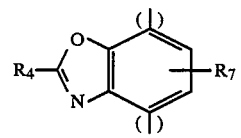
14.
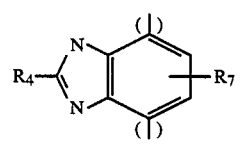
15.
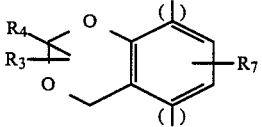
16.
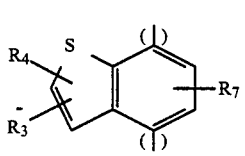
17.
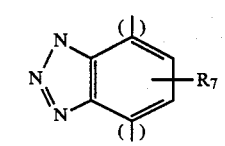
18.
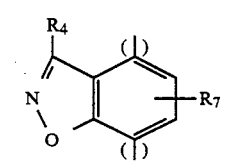
19.
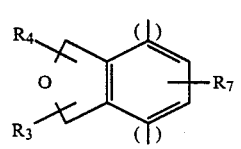
20.
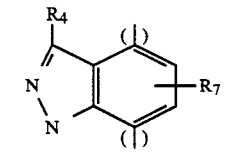
21.
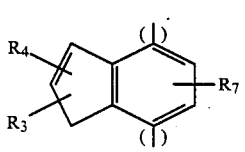

22. 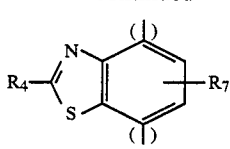

with the proviso that groups of the formulae 2, 5, 6, 9, 10, 11 and 15 may be bonded to the nitrogen atom of the piperazine group via position 5 or 8, the group to formula 4 may be bonded to the nitrogen atom of the piperazine group via position 6 or 9, and the groups of formulae 7, 8, 12, 13, 14 and 16–22 may be bonded to the nitrogen atom of the piperazine group via position 4 or 7, in which $R_3$ represents hydrogen or straight or branched alkyl having 1 to 3 carbon atoms, $R_4$ represents hydrogen, halogen, alkyl having 1 to 3 carbon atoms, methylene, ethylidene or vinyl, a straight or branched hydroxyalkyl having 1 to 3 carbon atoms, which may optionally be etherified or esterified, or an alkylcarbonyl having 1 to 3 carbon atoms in the straight or branched alkyl, and an oxo or a phenyl, and $R_7$ is hydrogen or fluorine;

A is a straight or branched alkylene having 2 to 10 carbon atoms;

B is an aryl or a heteroaryl which may be substituted with one or more substituents selected from the group consisting of: halogen, trifluoromethyl, nitrile, alkoxy having 1 to 3 carbon atoms, hydroxy, esterified hydroxy, or alkyl having 1 to 2 carbon atoms, or wherein B is a straight or branched alkyl group or a saturated or partly unsaturated cycloalkyl group having 4 carbon atoms, or a pharmaceutically acceptable acid addition salt thereof, is administered to a patient in need thereof.

2. A method as defined in claim 1, wherein the active ingredient is employed in an amount between 0.1 and 100 mg/kg.

* * * * *